(12) United States Patent
Iwawaki et al.

(10) Patent No.: US 7,794,855 B2
(45) Date of Patent: Sep. 14, 2010

(54) COMPOUND AND ORGANIC LIGHT-EMITTING ELEMENT

(75) Inventors: Hironobu Iwawaki, Yokohama (JP); Chika Negishi, Yokosuka (JP); Shinjiro Okada, Kamakura (JP); Takao Takiguchi, Tokyo (JP); Akihiro Senoo, Kawasaki (JP); Masashi Hashimoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 657 days.

(21) Appl. No.: 11/737,798

(22) Filed: Apr. 20, 2007

(65) Prior Publication Data

US 2007/0249878 A1 Oct. 25, 2007

(30) Foreign Application Priority Data

Apr. 25, 2006 (JP) ............................. 2006-120805

(51) Int. Cl.
*H01L 51/54* (2006.01)
(52) U.S. Cl. .................... 428/690; 428/917; 313/504; 313/506
(58) Field of Classification Search ............... None
See application file for complete search history.

(56) References Cited

U.S. PATENT DOCUMENTS

| 7,241,513 | B2 | 7/2007 | Suzuki et al. | 428/690 |
| 2005/0236974 | A1 | 10/2005 | Suzuki et al. | 313/504 |
| 2006/0068221 | A1 | 3/2006 | Saitoh et al. | 428/690 |
| 2006/0097227 | A1 | 5/2006 | Okajima et al. | 252/301.16 |
| 2006/0121312 | A1 | 6/2006 | Yamada et al. | 428/690 |
| 2007/0063189 | A1 | 3/2007 | Schwalm et al. | 257/40 |
| 2007/0252141 | A1 | 11/2007 | Negishi et al. | 257/40 |

FOREIGN PATENT DOCUMENTS

| JP | 10-189248 | 7/1998 |
| JP | 2002-043058 | 2/2002 |
| JP | 2007-302650 | 11/2007 |
| WO | WO 02/20693 | 3/2002 |
| WO | WO 2005-026088 | 3/2005 |
| WO | WO 2005/105950 A1 * | 11/2005 |
| WO | WO 2007/072889 | 6/2007 |

OTHER PUBLICATIONS

Vincett et al., "Electrical Conduction and Low Voltage Blue Electroluminescence in Vacuum-Deposited Organic Films" *Thin Solid Films*, vol. 94, 171-183 (1982).

Chen et al., "Recent Developments in Molecular Organic Electroluminescent Materials," *Macromol. Symp.*, vol. 125, 1-48 (1997).

Burroughes et al., "Light-Emitting Diodes Based on Conjugated Polymers," *Nature*, vol. 347, 539-541 (1990).

(Continued)

*Primary Examiner*—Dawn Garrett
(74) *Attorney, Agent, or Firm*—Fitzpatrick, Cella, Harper & Scinto

(57) ABSTRACT

A high-performance organic light-emitting element and a novel organic compound realizing the above element are provided. A fluoranthene compound having a specific structure and an organic light-emitting element using the same are provided.

2 Claims, 1 Drawing Sheet

OTHER PUBLICATIONS

Kajigaeshi et al., "Halogenation Using Quaternary Ammonium Polyhalides. XIV. Aromatic Bromination and Iodination of Arenes by Use of Benzyltrimethylammonium Polyhalides-Zinc Chloride System," *Bull. Chem. Soc. Jpn.*, vol. 62, 439-443 (1989).

Search Report dated Apr. 8, 2008 in JP 01-10035326.

Partial Translation of JP 10-189248, published Jul. 21, 1998, claims 1-6, paragraphs [0014, 0017].

Partial Translation of JP 2002-043058, claim 1, published Feb. 8, 2002.

Partial Translation of WO 02/20693, published Mar. 14, 2002, claims 6, 8.

* cited by examiner

COMPOUND AND ORGANIC LIGHT-EMITTING ELEMENT

BACKGROUND OF THE INVENTION

1. Field of the Invention

The present invention relates to light-emitting elements using an organic compound, and more particularly, relates to a compound having a molecular structure represented by general formula (1) shown below and an organic electroluminescent (EL) element having stable high efficiency by using the above compound for a light-emitting layer or a charge transport layer.

2. Description of the Related Art

In the past, light emission was typically performed by applying a voltage to an anthracene-deposited film (Thin Solid Films, 94 (1982) 171).

In addition, as particularly described in Macromol. Symp. 125, 1 to 48 (1997), typically, an organic EL element has a structure in which top and bottom electrodes are formed on a transparent substrate and organic material layers, including a light-emitting layer, are provided between the electrodes.

In addition, when various types of fluorescent organic compounds are used, light emission from ultraviolet to infrared can be performed, and, in recent years, research on various compounds have been intensively pursued.

Furthermore, besides organic light-emitting elements using a relatively low molecular weight material as described above, an organic light-emitting element using a conjugated polymer was reported by one group at Cambridge University in Nature, 347, 539 (1990). According to this report, it was confirmed that light emission was obtained from a monolayer film of polyphenylene vinylene (PPV) formed by a coating system.

Based on the recent advances in organic light-emitting elements in which thin and lightweight light-emitting devices have been produced which are characterized by a high luminance at a low applied voltage, a wide spectrum of light-emitting wavelengths, and a high-speed response, it was expected that a wide range of applications of the organic light-emitting element would be realized.

However, it has proven necessary to further improve luminance and/or conversion efficiency. In addition, there have been many problems in durability, such as changes in performance after long term use and degradation thereof caused, for example, by an oxygen-containing gas and/or moisture. Furthermore, when a light-emitting element is applied to a full-color display and the like, light emission of blue, green, and red having superior color purity is required. However, for this application, present device performances have not been satisfactory.

In addition, as a fluorescent organic compound used for an electron transport layer and a light-emitting layer, a large number of aromatic compounds and condensed polycyclic aromatic compounds have been investigated. However, a material having entirely satisfactory light-emission luminance and durability has not been obtained.

Documents bearing on application of fluoranthene compounds to organic EL elements include, Japanese Patent Laid-Open No. 10-189248, and, WO2005026088. Such documents disclose an organic compound having a fluoranthene ring and two biphenyl groups bonded thereto. However, an organic compound of the present invention, which is formed of a fluoranthene ring and a linearly linked oligophenylene group, has believed to be unknown.

When an organic EL element is applied to a display apparatus and the like, apart from high efficiency and highly luminant light emission, sufficient durability must be ensured. However, the above requirements have not been presently sufficiently satisfied.

SUMMARY OF THE INVENTION

The present invention provides a novel compound used for organic EL elements, that has a molecular structure represented by the following general formula (1) and an organic EL element using the same, that has highly efficient and highly luminant light emission. In addition, the present invention provides an organic EL element having high durability. Furthermore, the present invention also provides an organic EL element that can be easily manufactured and that can be formed at a relatively low cost.

According to the present invention, a compound represented by the following general formula (1) is provided.

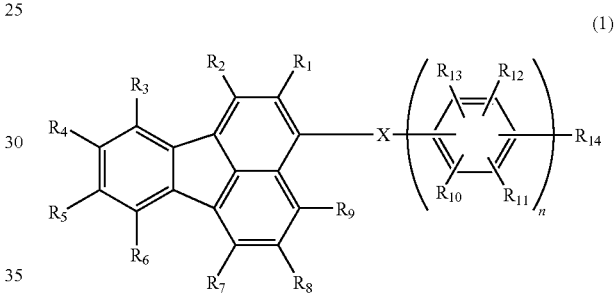

In the above formula, X represents an unsubstituted phenylene group, and $R_1$ to $R_{14}$ each independently represent a hydrogen atom, a halogen atom, a substituted or an unsubstituted amino group, or a linear, a branched, or a cyclic alkyl group having 1 to 20 carbon atoms. In the alkyl group, one methylene group or at least two methylene groups which are not adjacent to each other may be substituted with —O—, at least one methylene group may be substituted with an arylene group or a divalent heterocyclic group, and a hydrogen atom of the alkyl group may be substituted with a fluorine atom. $R_1$ to $R_{14}$ may be the same or may be different from each other. In the above formula, n represents an integer of from 1 to 10.

A light-emitting element using the compound of the present invention as a dopant of a light-emitting layer is provided with superior light emission efficiency. In addition, as a light-emitting material, the compound of the present invention exhibits superior color purity.

Further features of the present invention will become apparent from the following description of exemplary embodiments with reference to the attached drawings.

DESCRIPTION OF THE EMBODIMENTS

Figure 1A:
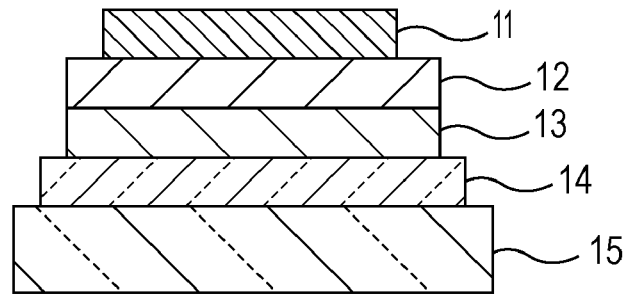
FIGS. 1A to 1C are views each showing a different example of a light-emitting element according to the present invention.

A compound according to the present invention is a compound represented by the following general formula (1).

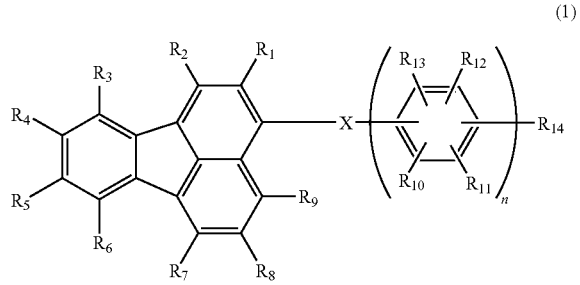

In the above formula, X represents an unsubstituted phenylene group, and $R_1$ to $R_{14}$ each independently represent a hydrogen atom, a halogen atom, a substituted or an unsubstituted amino group, or a linear, a branched, or a cyclic alkyl group having 1 to 20 carbon atoms. In the above alkyl group, one methylene group or at least two methylene groups which are not adjacent to each other may be substituted with —O—, at least one methylene group may be substituted with an arylene group or a divalent heterocyclic group, and a hydrogen atom of the alkyl group may be substituted with a fluorine atom. $R_1$ to $R_{14}$ may be the same or may be different from each other. In the above formula, n represents an integer of from 1 to 10.

In addition, the X in the above general formula (1) preferably represents an unsubstituted 1,4 phenylene group.

In addition, in an organic light-emitting element formed of a pair of electrodes, that is, an anode and a cathode, at least one of which is transparent or semi-transparent. One or at least two organic compound layers are provided between the electrodes. At least one of the organic compound layers includes at least one type of organic compound represented by the above general formula (1).

In addition, in the organic light-emitting element described above, at least one layer of the organic compound layers is a light-emitting layer and includes at least one type of compound represented by the above general formula (1).

In addition, in the above organic light-emitting element, the compound represented by the above general formula (1) can be a guest material of the light-emitting layer.

In addition, in the organic light-emitting element described above, the compound represented by the above general formula (1) can be a host material of the light-emitting layer.

In addition, in the organic light-emitting element described above, the host material and the guest material of the light-emitting layer are each independently the compound represented by the above general formula (1).

When the light-emitting layer is formed of carrier-transporting host and guest materials, a primary process resulting in light emission includes the following steps:
1. Transportation of electrons and holes in a light-emitting layer;
2. Generation of excitons of host;
3. Transmission of excited energy between host molecules; and
4. Transfer of excited energy from host to guest.

Desired energy transfer and light emission in the individual steps occur competitively with various deactivation steps.

In order to enhance light emission efficiency of an EL element, of course, a light-emitting center material itself preferably has a high light emission quantum yield. In addition, it is also very important to efficiently perform energy transfer between host materials and between host and guest materials. Although the reason for degradation in light emission by current application has not been clearly understood, it is believed that the degradation is at least associated with the light-emitting center material, itself, or the change in environment of the light-emitting material caused by molecules present therearound.

One of the reasons causing degradation in light emission by current application is the mobility of the host in the light-emitting layer. When conjugated surfaces of molecules forming the light-emitting layer are not significantly overlapped with each other due to molecular or steric constraints, mobility is decreased, and drive voltage is increased. In addition, as a result, injection properties may be degraded in some cases. To avoid these problems, it is important to design molecular structure so that molecules overlap each other. For example, a benzene ring, a naphthalene ring, an anthracene ring, a phenanthrene ring, a fluorene ring, a carbazole ring, and an indole ring are generally used for this purpose.

In addition, the guest molecule must have a structure of a high quantum yield, and such structure of high quantum yield must be introduced in a condensed ring portion. In general, the quantum yield is used as an index indicating the efficiency of converting excited energy into light. In the compound according to the present invention, a fluoranthene structure of a high quantum yield corresponds to a condensed ring portion.

Through intensive research carried out by the present inventors, it was found that when a compound represented by the above general formula (1) is preferably used for the charge transport layer and the light-emitting layer of an organic EL element and is also preferably used as a host and guest of the light-emitting layer, a light-emitting element can be realized that has high light emission efficiency, maintains high luminance for a long period of time, and exhibits less degradation caused by current application.

The compound of the present invention has an oligophenylene portion that serves as a portion generating "overlapping of conjugated surfaces" which is required for the host, and has a fluoranthene portion as a portion which is expected to have a high quantum yield as the guest molecule. Hence, the compound of the present invention may be used for both the host and the guest of the light-emitting layer. In this case, as reasons why the oligophenylene group is selected as the portion generating overlapping of conjugate surfaces, the following may be mentioned. The oligophenylene group is advantageous since it is less expensive than other aromatic rings; and when employed as a guest molecule for blue light emission, the wavelength can be shortened and improvement in color purity is further expected as compared to that of other condensed rings. As the oligophenylene group, a biphenylene group, a terphenylene group, and a quarterna-phenylene group are typical with the biphenylene group and terphenylene group being more preferable. In formula (1) the oligophenylene group is constituted of the constituents on the right side of the formula, which both include "X" and the substituted or unsubstituted phenylene where n is from 1 to 10.

As noted above the general formula (1), $R_1$ to $R_{14}$ are each independently selected from a hydrogen atom, a halogen atom, a substituted or an unsubstituted amino group, or a linear, a branched, or a cyclic alkyl group having 1 to 20 carbon atoms. In the alkyl group, one methylene group or at least two methylene groups which are not adjacent to each other may be substituted with —O—, at least one methylene group may be substituted with an arylene group or a divalent heterocyclic group, and a hydrogen atom of the alkyl group may be substituted with a fluorine atom. $R_1$ to $R_{14}$ may be the same or may be different from each other. In addition, $R_1$ to $R_{14}$ each preferably represent a hydrogen atom, a halogen atom, or a linear alkyl group having 1 to 10 carbon atoms. In the alkyl group, one methylene group or at least two methylene groups which are not adjacent to each other may be substituted with —O—, and a hydrogen atom of the alkyl group may be substituted with a fluorine atom. More preferably $R_1$ to $R_{14}$ each represent a hydrogen atom, a fluorine atom, or a linear alkyl group having 1 to 5 carbon atoms in which one methylene group of the alkyl group may be substituted with —O—, and a hydrogen atom of the alkyl group may be substituted with a fluorine atom.

The compound of the present invention can be effectively used for the light-emitting layer as described above; however, it can also be effectively used for an electron transport layer, a hole transport layer, an electron blocking layer, a hole blocking layer, an electron injection layer, and a hole injection layer.

When an organic layer containing the compound of the present invention is formed, for example, a vacuum evaporation method, a casting method, a coating method, a spin coating method, and an ink-jet method may be used.

Figure 1B:
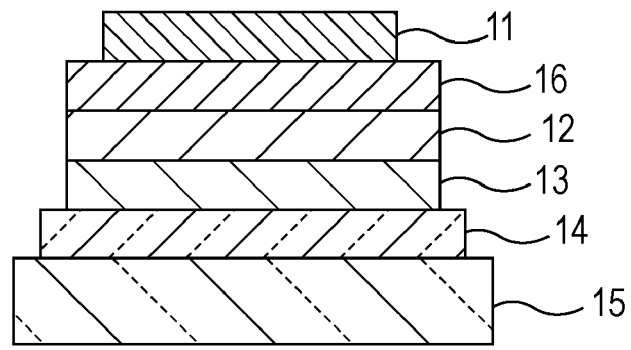
Figure 1C:
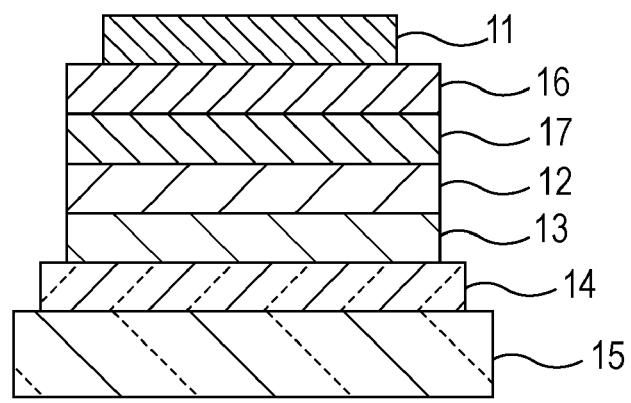

A basic element structure of the present invention is shown in FIGS. 1A, 1B, and 1C. First, reference numerals in the figure will be described. Reference numeral 11 indicates a metal electrode, reference numeral 12 a light-emitting layer, reference numeral 13 a hole transport layer, reference numeral 14 a transparent electrode, reference numeral 15 transparent substrate, reference numeral 16 an electron transport layer, and reference numeral 17 an exciton diffusion preventing layer.

As shown in FIGS. 1A to 1C, in general, an organic EL element has the structure in which on the transparent substrate 15, the transparent electrode 14 having a thickness of 50 to 200 nm, a plurality of organic layers, and the metal electrode 11 are formed in that order from bottom to top.

In FIG. 1A, an example is shown in which the light-emitting layer 12 and the hole transport layer 13 are formed as the organic layers. As the transparent electrode 14, for example, ITO having a large work function is used, and hence hole injection can be easily performed from the transparent electrode 14 to the hole transport layer 13. The metal electrode 11 is formed using a material such a metal having a small work function, such as aluminum, magnesium, or an alloy thereof. Hence electron injection into the organic layer can be easily performed.

In another embodiment the light-emitting layer 12 is formed using the compound of the present invention and, for the hole transport layer 13, a material having electron-donating properties, such as a triphenydiamine derivative represented by α-NPD, may also be used.

The element thus formed according to FIG. 1A has electrical rectification properties, and when an electric field is applied thereto so that the metal electrode 11 and the transparent electrode 14 function as a cathode and an anode, respectively, electrons are injected into the light-emitting layer 12 from the metal electrode 11, and holes are injected from the transparent electrode 14.

The holes and electrons thus injected are recombined in the light-emitting layer 12 to generate excitons, thereby emitting light. At this stage, the hole transport layer 13 functions as an electron blocking layer. Accordingly, the recombination efficiency at the interface between the light-emitting layer 12 and the hole transport layer 13 is improved, so that the light emission efficiency is improved.

In FIG. 1B, an electron transport layer 16 is provided between the metal electrode 11 and the light-emitting layer 12. The light emission function is thereby separated from the electron- and the hole-transport functions to form a more effective carrier blocking structure, so that the light emission efficiency is improved. A compound for the electron transport layer 16, for example, is an oxadiazole derivative.

In FIG. 1C, a four-layer structure is illustrated as a preferable embodiment which is constituted of hole transport layer 13, light-emitting layer 12, exciton diffusion preventing layer 17, electron transport layer 16, and the metal electrode 11 provided in that order on the transparent electrode 14 used as the anode.

Exemplary structural formulas of the organic compounds used in the present invention are shown below. However, the formulas shown below are merely typical examples, and it is to be understood that the present invention is not limited thereto at all.

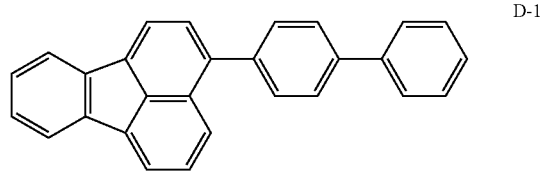

D-1

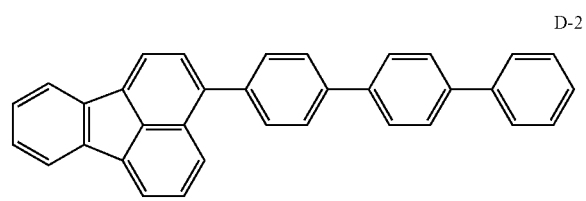

D-2

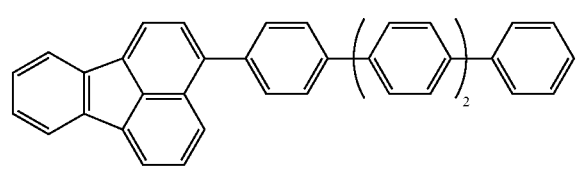

D-3

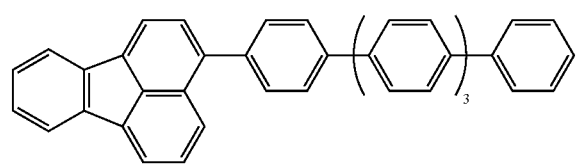

D-4

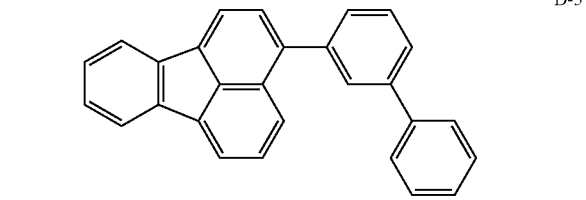

D-5

-continued
D-6
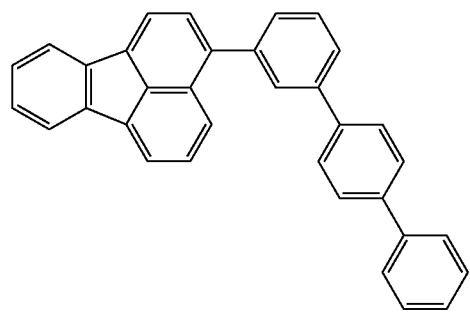
D-12
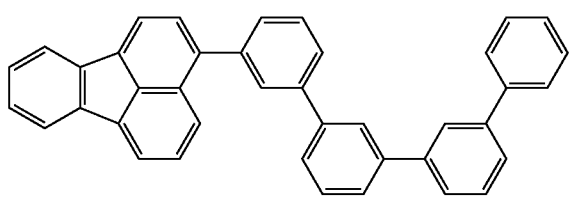
D-7
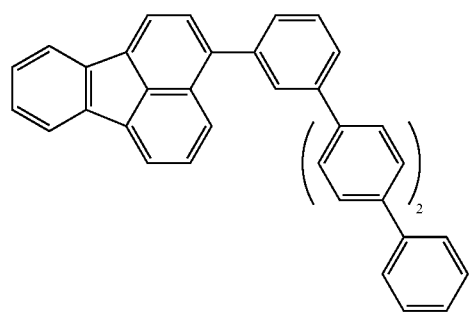
D-13
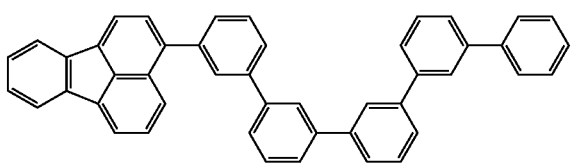
D-8
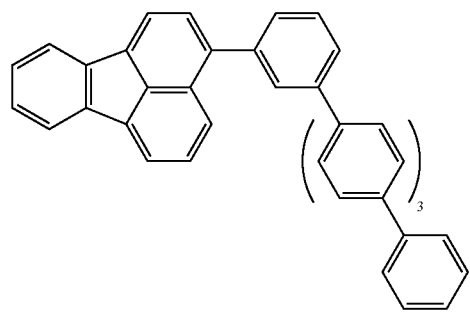
D-14
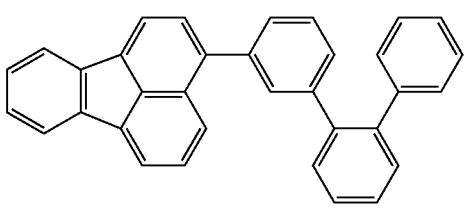
D-9
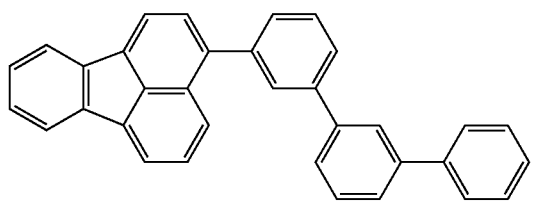
D-15
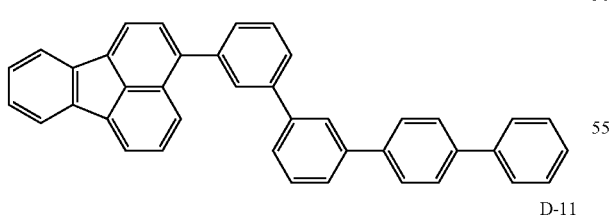
D-10
D-11
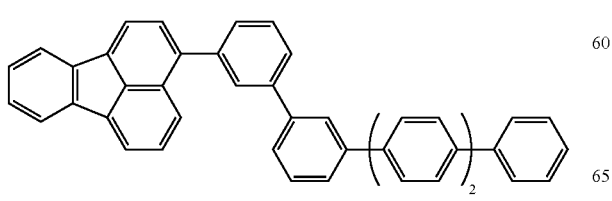
D-16
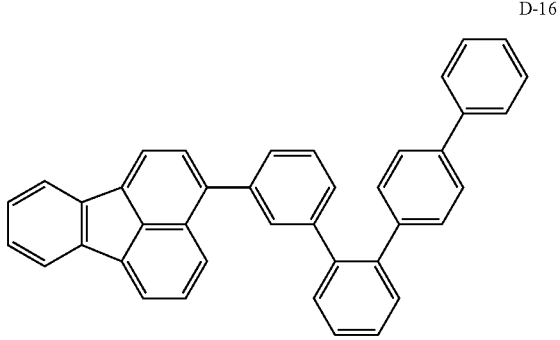

-continued
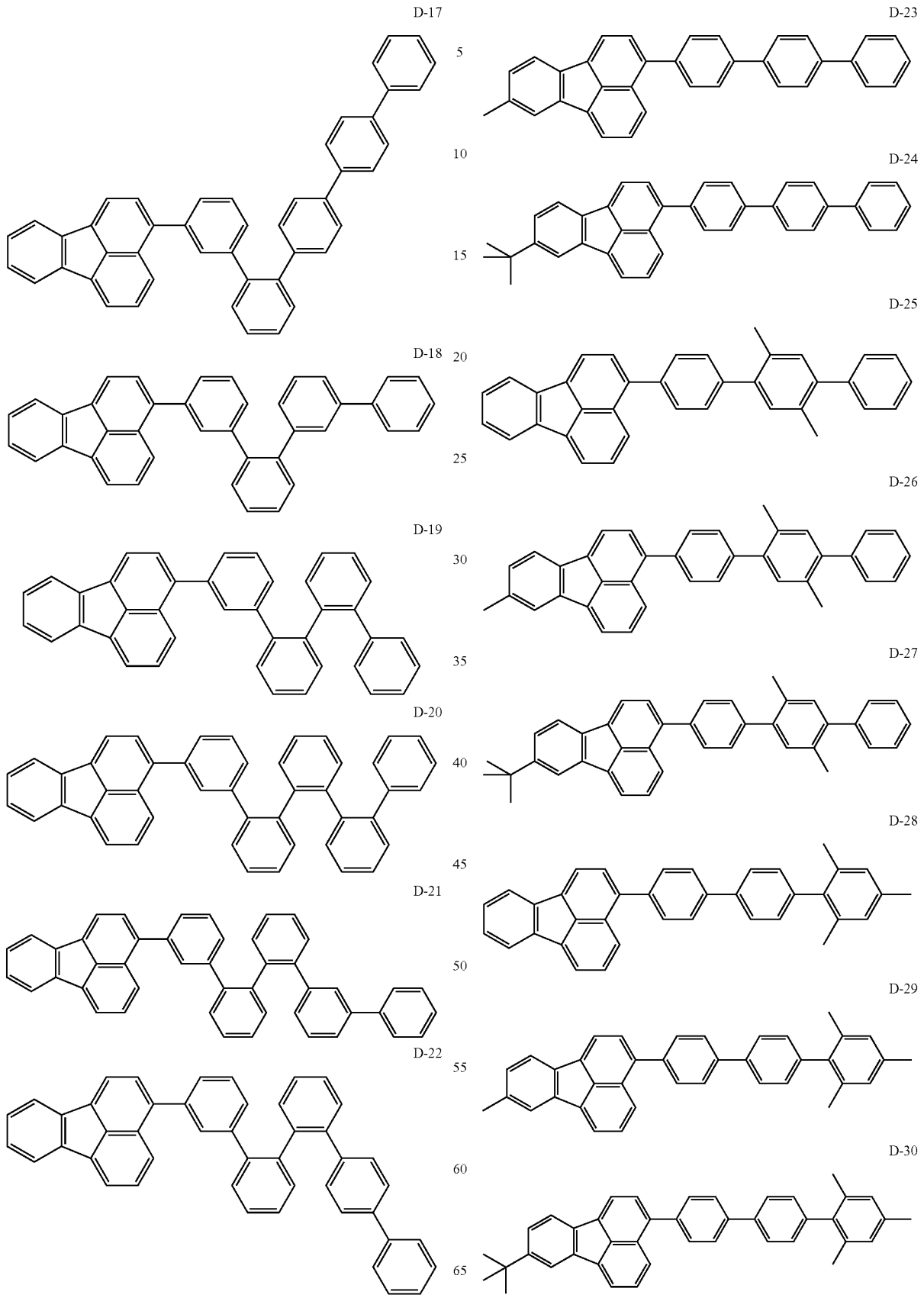

-continued
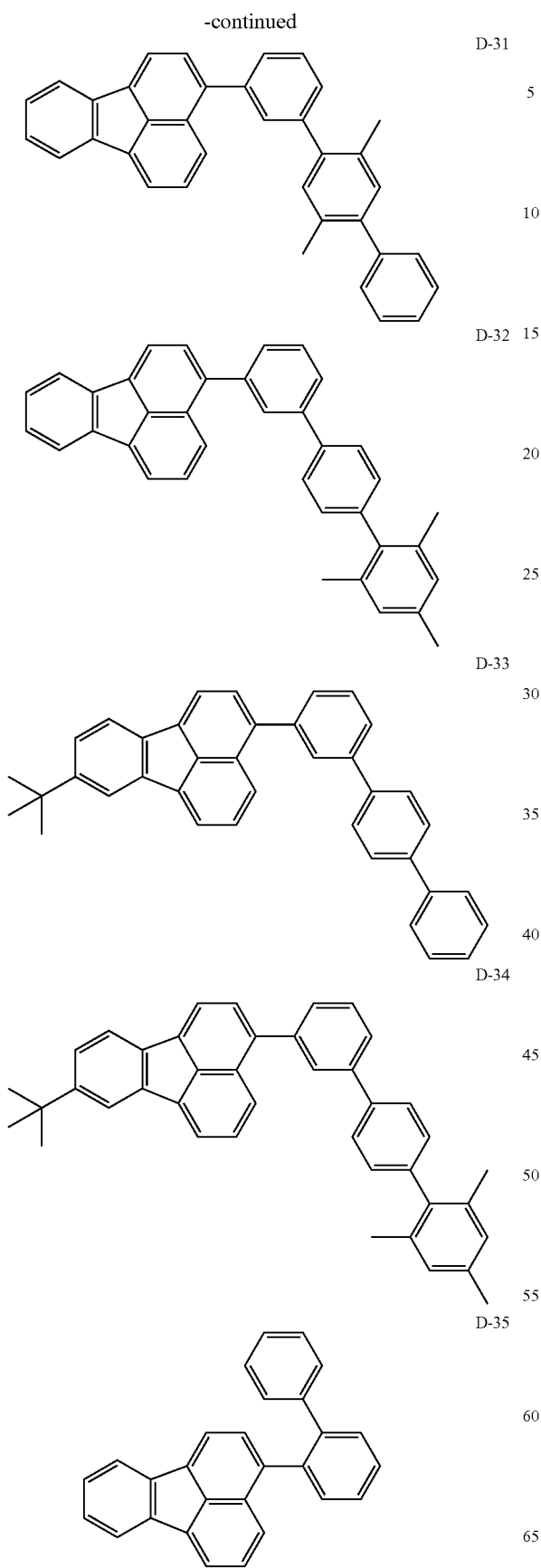
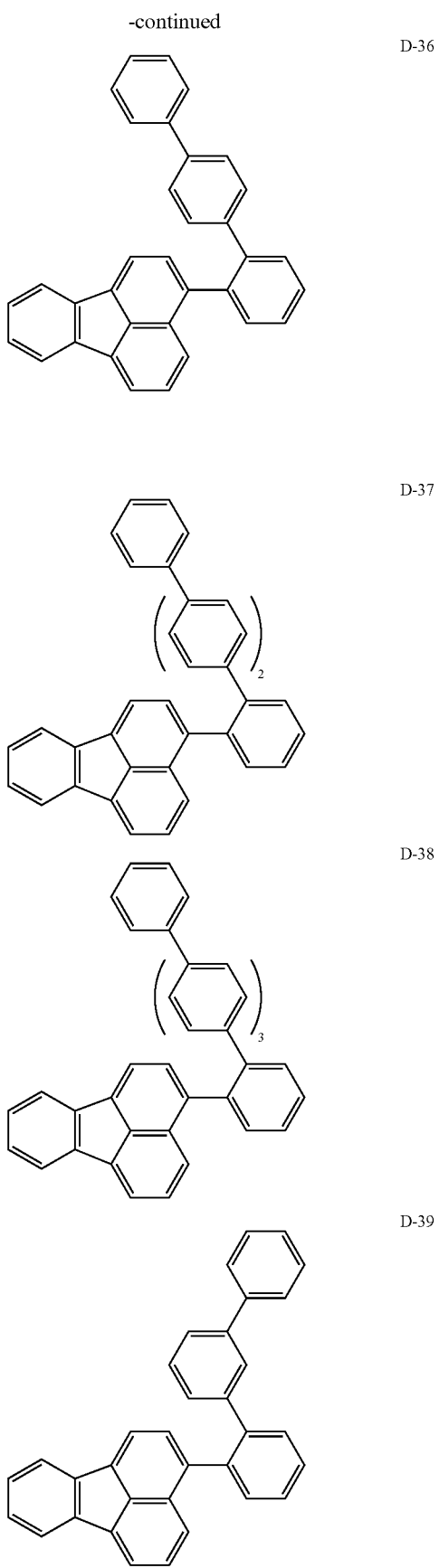

-continued
D-40
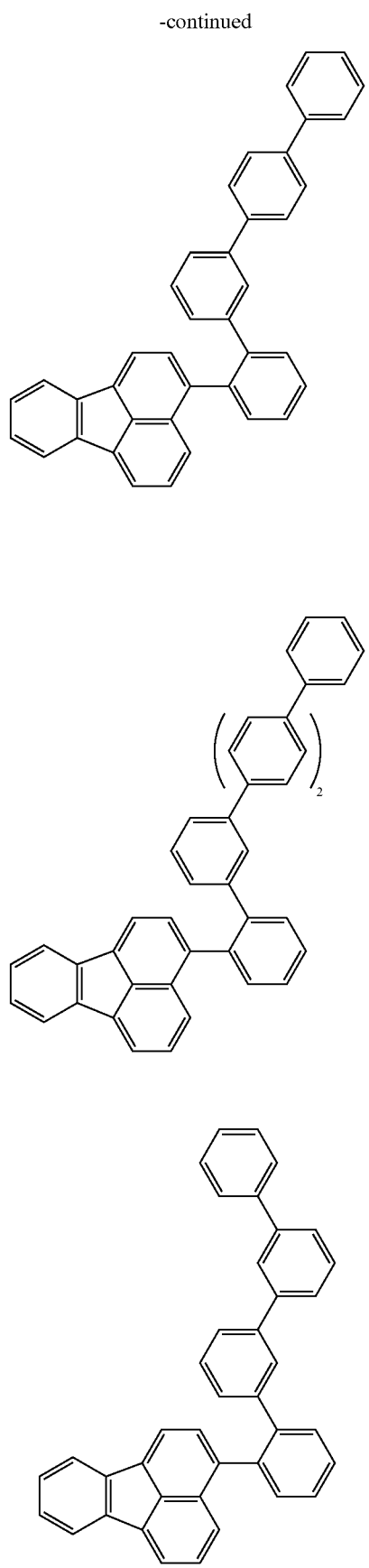
D-41
D-42
-continued
D-43
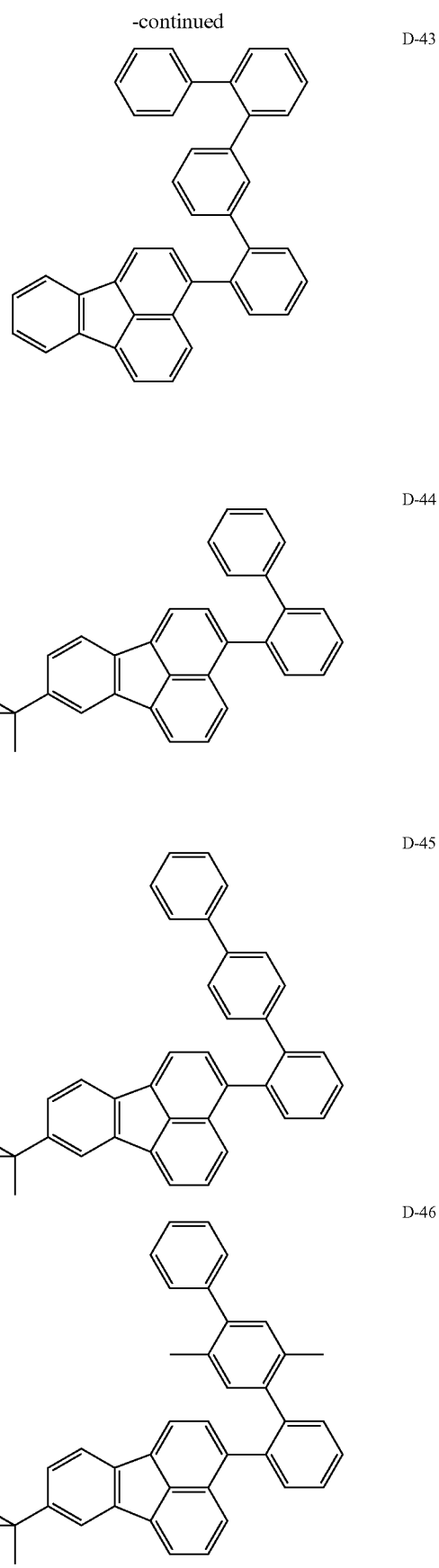
D-44
D-45
D-46

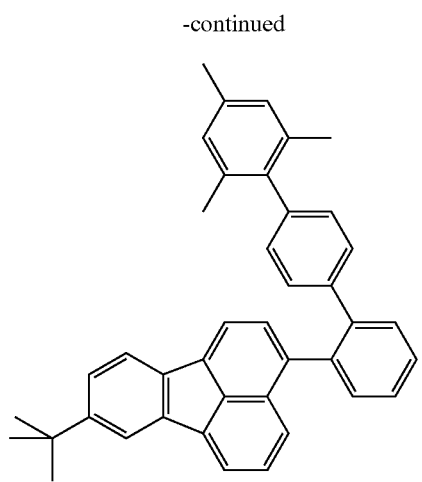
D-47
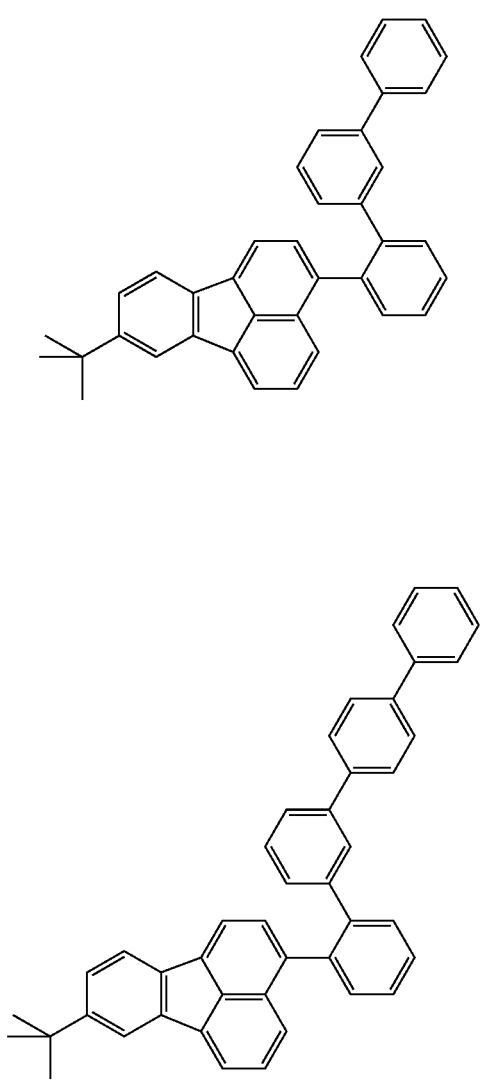
D-48
D-49
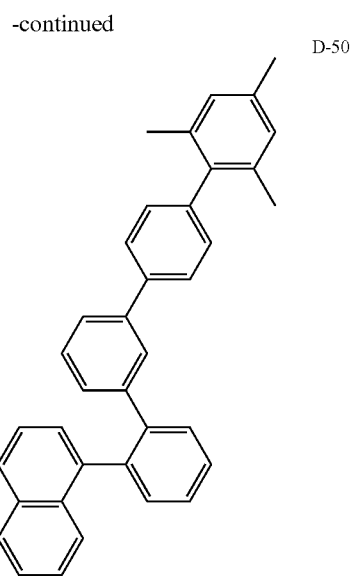
D-50
D-51
D-52
D-53

-continued

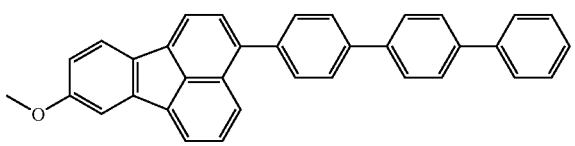
D-54

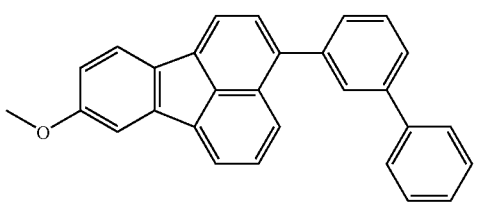
D-55

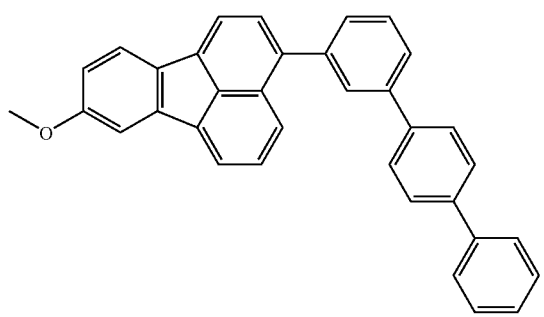
D-56

EXAMPLES

Hereinafter, the present invention will be described in detail with reference to the examples. However, the present invention is not limited thereto.

First, with reference to Bull. Chem. Soc. Jpn. 62, (1989), 439, 3-halogeno-fluoranthene was synthesized. In addition, by using 3-halogeno-fluoranthene thus obtained, with reference to Organic Syntheses Via Boranes Volume 3, boronic acid or a boronic pinacol ester was synthesized. By using the compounds thus obtained, Suzuki coupling (Organic Syntheses Via Boranes Volume 3), halogenation (Bull. Chem. Soc. Jpn. 62, (1989), 439), and boronic acid synthesis were optionally performed in combination, thereby synthesizing the following reaction intermediate product. The disclosure of each of the above referenced articles is incorporated herein by reference.

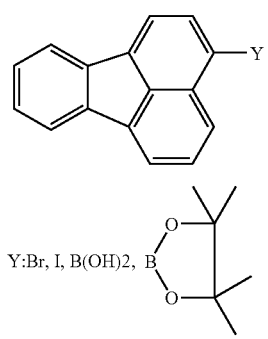

Y:Br, I, B(OH)2, B

In the above formula, Y represents one of the groups shown above. In addition, the compound of the present invention can be synthesized by a Suzuki Coupling reaction using the above fluoranthene derivative, a halogenated benzene derivative, and benzene boronic acid derivative, which are optionally mixed in combination.

Example 1

Synthesis of Exemplified Compound No. D-2

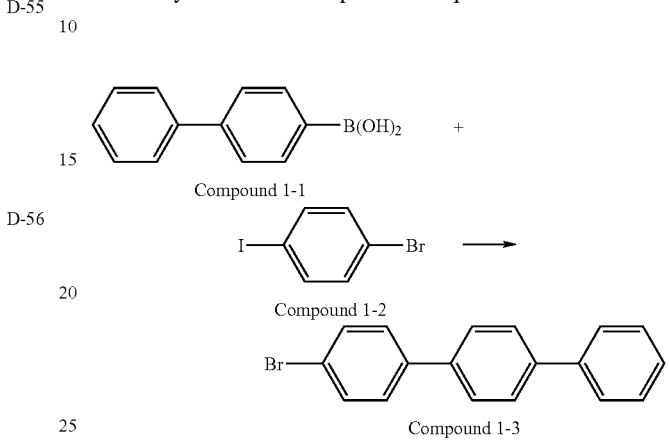

The compound 1-1 (manufactured by Aldrich Chemical Company, Inc.) in an amount of 344 mg (2 mmole), 566 mg (2 mmole) of the compound 1-2, 40.1 g of Pd (PPh$_3$), 10 ml of toluene, 5 ml of ethanol, and 10 ml of an aqueous sodium carbonate solution at a concentration of 2 M were charged in an eggplant flask having a volume of 100 ml and were then stirred for 8 hours at 40° C. under a nitrogen stream. After the reaction was completed, crystals were obtained by filtration, followed by washing using water, ethanol, and toluene. The crystals thus obtained were dried by evacuation at 120° C., so that 340 mg (at a yield of 60%) of the compound 1-3 was obtained.

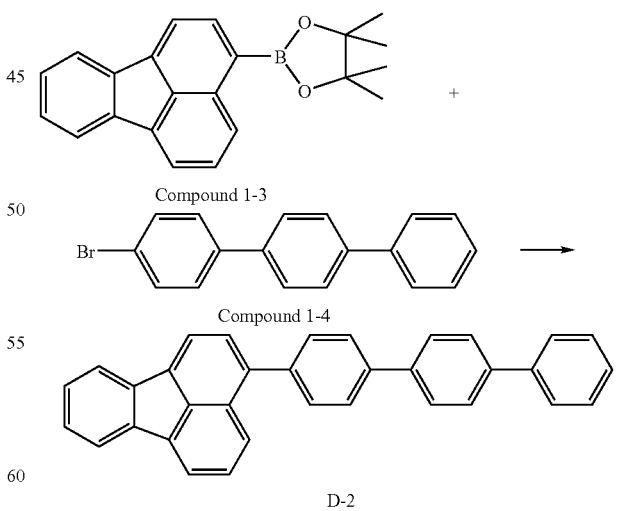

The compound 1-3 in an amount of 800 mg (2.44 mmole), 830 mg (2.68 mmole) of the compound 1-4, 40.05 g of Pd (PPh$_3$), 10 ml of toluene, 5 ml of ethanol, and 10 ml of an aqueous sodium carbonate solution at a concentration of 2 M were charged in an eggplant flask having a volume of 100 ml and were then stirred for 8 hours at 80° C. under a nitrogen stream. After the reaction was completed, crystals which were obtained by filtration were washed using water, ethanol, and toluene. The crystals thus obtained were dried by evacuation at 120° C., so that 250 mg (at a yield of 78%) of the exemplified compound No. D-2 was obtained by sublimation purification.

By a matrix-assisted laser deposition ionization-time of flight type mass spectrometric (MALDI-TOF MA) analysis, a mass of 430.2 that was M+ of this compound was confirmed.

Comparative Example 1

Synthesis of Comparative Compound 2

The comparative compound 2 was synthesized in a manner similar to that of Example 1 except that compound 1-5 was used instead of the compound 1-4 of Example 1.

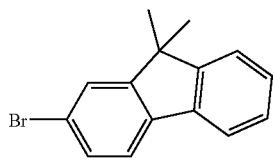

Compound 1-5

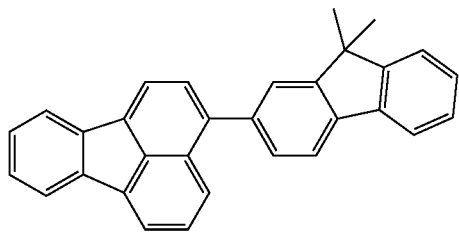

Comparative Compound 2

Comparative Example 2

Synthesis of Comparative Compound 3

The comparative compound 3 was synthesized in a manner similar to that of Example 1 except that compound 1-6 was used instead of the compound 1-4 of Example 1.

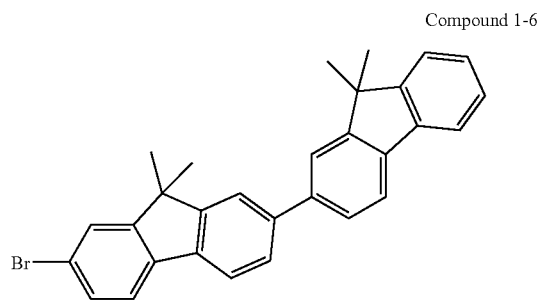

Compound 1-6

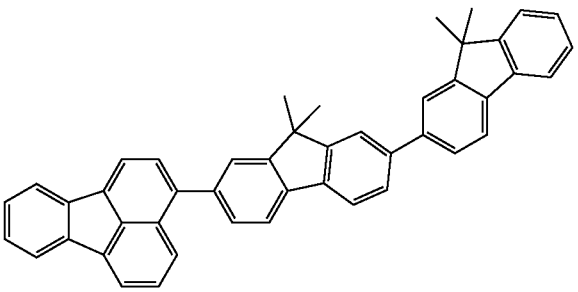

Comparative Compound 3

The photoluminescence (PL) properties of the above compounds were investigated, and the results thereof are shown in Table 1.

TABLE 1

|  | Compound | λ1 (nm) | λmax (nm) |
|---|---|---|---|
| Example 1 | Exemplified compound D-2 | 415 | 461 |
| Comparative Example 1 | Comparative compound 2 | 417 | 465 |
| Comparative Example 2 | Comparative compound 3 | 419 | 466 |

Note:
The maximum light-emitting wavelength of the light emission spectrum is represented by λmax, and a rising part (emission intensity being one tenth of that of λmax) at a short wavelength side of λmax is represented by λ1.

It is found that when the results in Table 1 are compared to each other, the short wavelength component of the exemplified compound D-2 is more intense as compared to that of the comparative compounds 2 and 3, and that λmax is also shorter than that thereof. From this comparison, it can be said that although the comparative compound 2 (fluorenyl-fluoranthene) and the comparative compound 3 (bifluorenyl-fluoranthene) are sufficient as a blue light emission material, the exemplified compound D-2 (o-terphenyl-fluoranthene) is superior in terms of color purity as a blue light emission material.

Example 2

In this example, an element having the three organic layers shown in FIG. 1B was used. An ITO film having a thickness of 100 nm was patterned on a glass substrate. On this ITO substrate, the following organic layers and the electrode layer were sequentially formed in a vacuum chamber at a pressure of $10^{-5}$ Pa by vacuum evaporation using resistance heating so as to obtain a facing electrode area of 3 mm$^2$.

Hole transport layer (40 nm): Compound 2

Light-emitting layer (50 nm): Compound 3 and the exemplified compound D-2 (weight ratio of 5%)

Electron transport layer (25 nm): Compound 4

Metal electrode layer 1 (0.5 nm): LiF

Metal electrode layer 2 (100 nm): Al

Compound 2

Compound 3

Compound 4

As for properties of the EL element, current-voltage properties were measured by an ammeter 4140B manufactured by Hewlett-Packard Co., and the light emission luminance was measured by BM7 manufactured by Topcon Corp. It was confirmed that the element of this example is a blue light emission element at a wavelength of 465 nm. The luminance and the light emission efficiencies were 6.5 cd/A and 5.0 lm/W (at 400 cd/m$^2$), respectively. In addition, the current density at an application voltage of 5 V was 40 mA/cm$^2$.

Example 3

An element was formed in a manner similar to that in Example 2 except that the exemplified compound No. D-1 was used instead of the exemplified compound No. D-2 of Example 2. The element of this example was a blue light emission element, and the luminance and the light emission efficiencies were 6.4 cd/A and 4.9 lm/W (at 400 cd/m$^2$), respectively. In addition, the current density at an application voltage of 5 V was 39 mA/cm$^2$.

Example 4

An element was formed in a manner similar to that in Example 2 except that the exemplified compound No. D-5 was used instead of the compound 3 of Example 2. The element of this example was a blue light emission element, and the luminance and the light emission efficiencies were 5.0 cd/A and 4.0 lm/W (at 400 cd/m$^2$), respectively. In addition, the current density at an application voltage of 5 V was 50 mA/cm$^2$.

Example 5
Synthesis of Exemplified Compound No. D-1

The exemplified compound No. D-1 could be synthesized in a manner similar to that of Example 1 except that compound 1-7 was used instead of the compound 1-4 of Example 1.

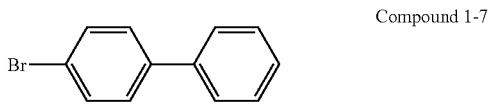

Compound 1-7

Example 6

Synthesis of Exemplified Compound No. D-5

The exemplified compound No. D-5 could be synthesized in a manner similar to that of Example 1 except that compound 1-8 was used instead of the compound 1-4 of Example 1.

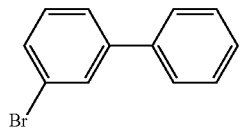

Compound 1-8

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-120805 filed Apr. 25, 2006, which is hereby incorporated by reference herein in its entirety.

What is claimed is:

1. An organic light-emitting element comprising:
    a pair of electrodes constituted by an anode and a cathode; and
    one or a plurality of organic compound layers provided between the electrodes, wherein the one or the plurality of organic compound layer is a light-emitting layer, the light-emitting layer is composed of a host material and a guest material, and a combination of the host material and the guest material is any one of combinations shown below:

a combination in which the host material is a compound represented by Compound 3 and

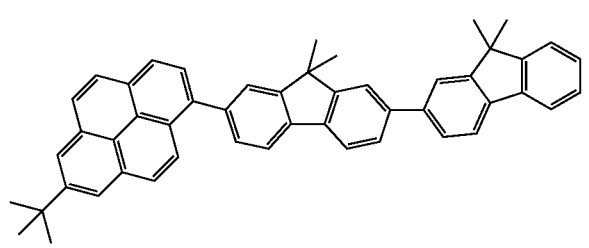

Compound 3 the guest material is a compound represented by Formula 2, or

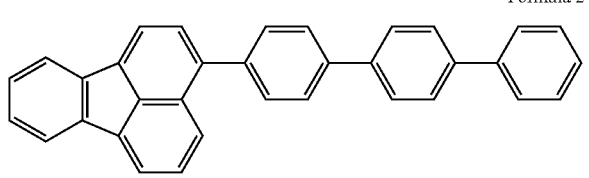

Formula 2 a combination in which the host material is a compound represented by Compound 3 and

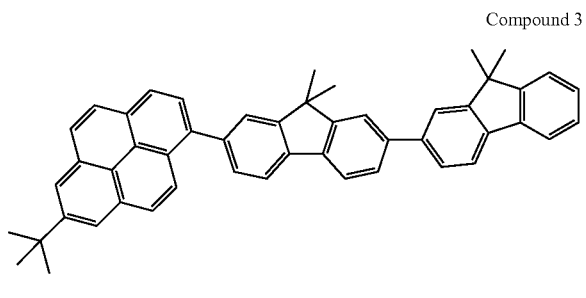

Compound 3 the guest material is a compound represented by the following structural formula, Formula 1, or

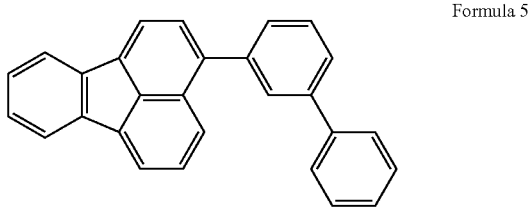

Formula 1 a combination in which the host material is a compound represented by the following structural formula, Formula 5, and

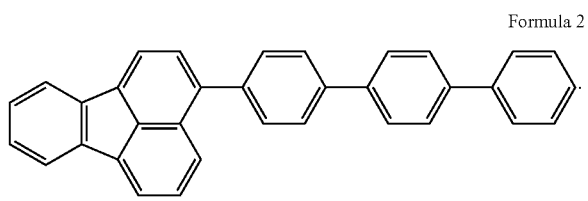

Formula 5 the guest material is a compound represented by the following structural formula, Formula 2, or Formula 2

2. The organic light-emitting element according to claim 1, wherein the plurality of organic compound layers comprise, other than the light-emitting layer, a hole transport layer and an electron transport layer, and wherein the hole transport layer comprises a compound represented by the following structural formula, Compound 2, and Compound 2
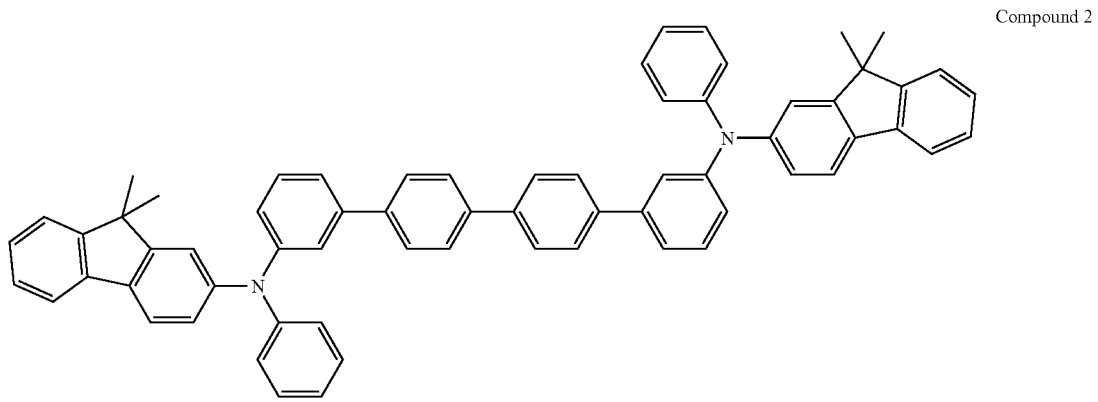
the electron transport layer comprises a compound represented by the following structural formula, Compound 4
Compound 4
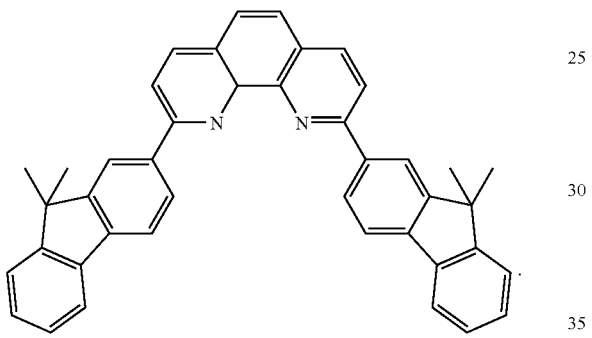
* * * * *